United States Patent

MacLeod et al.

Patent Number: 6,136,824
Date of Patent: Oct. 24, 2000

[54] 1-PIPERIDINYL-PROPAN-2-DERIVATIVES AND THEIR USE AS THERAPEUTIC AGENTS

[75] Inventors: Angus Murray MacLeod, Bishops Stortford; Christopher John Swain, Duxford; Monique Bodil van Niel, Welwyn Garden City, all of United Kingdom

[73] Assignee: Merck Sharp & Dohme Ltd., Hoddesdon, United Kingdom

[21] Appl. No.: 09/511,002

[22] Filed: Feb. 22, 2000

[30] Foreign Application Priority Data

Feb. 3, 1999 [GB] United Kingdom ............... 9904786

[51] Int. Cl.[7] ............................................. A01N 43/40
[52] U.S. Cl. ........................................ 514/317; 546/192
[58] Field of Search ........................... 546/190; 514/317

[56] References Cited

U.S. PATENT DOCUMENTS 3,014,912 12/1961 Petrow et al. ........................ 546/190
4,069,221 1/1978 Yonan .................................. 546/190

FOREIGN PATENT DOCUMENTS

94/10165 5/1994 WIPO .

*Primary Examiner*—Deborah C. Lambkin
*Attorney, Agent, or Firm*—J. Eric Thies; David L. Rose

[57] ABSTRACT

The present invention relates compounds of the formula (I):

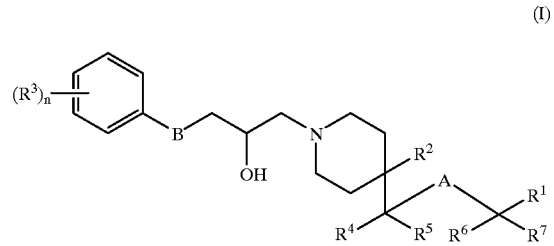

wherein
$R^1$ and $R^2$ each independently represents a phenyl group optionally substituted by a variety of substituents;
$R^3$ represents a variety of substituents;
$R^4$, $R^5$, $R^6$, and $R^7$ each independently represents hydrogen or $C_{1-6}$alkyl;
A represents —O— or —S—;
B represents —O—, —S—, —$NR^a$— or —$CHR^a$—; and
n is zero, 1, 2, 3, 4 or 5;
or a pharmaceutically acceptable salt or a prodrug thereof.

The compounds are of particular use in the treatment or prevention of depression, anxiety, pain, inflammation, migaine, emesis or postherpetic neuralgia.

28 Claims, No Drawings

1-PIPERIDINYL-PROPAN-2-DERIVATIVES AND THEIR USE AS THERAPEUTIC AGENTS

This invention relates to a novel class of 1-piperidinyl-propan-2-ol derivatives which are useful in the treatment of depression and/or anxiety.

Major depression is characterised by feelings of intense sadness and despair, mental slowing and loss of concentration, pessimistic worry, agitation, and self-deprecation. Physical changes also ocur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

Treatment regimens commonly include the use of tricyclic antidepressants, monoamine oxidase inhibitors, some psychotropic drugs, lithium carbonate, and electroconvulsive therapy (ECT) (see R. J. Baldessarini in *Goodman & Gilman's The Pharmacological Basis of Therapeutics*, 9th Edition, Chapter 19, McGraw-Hill, 1996 for a review). More recently, new classes of antidepressant drugs are being developed including selective serotonin reuptake inhibitors (SSRIs), specific monoamine reuptake inhibitors and $5\text{-}HT_{1A}$ receptor agonists, antagonists and partial agonists.

Anxiety is an emotional condition characterised by feelings such as apprehension and fear accompanied by physical symptoms such as tachycardia, increased respiration, sweating and tremor. It is a normal emotion but when it is severe and disabling it becomes pathological.

Anxiety disorders are generally treated using benzodiazepine sedative-antianxiety agents. Potent benzodiazepines are effective in panic disorder as well as in generalised anxiety disorder, however, the risks associated with drug dependency may limit their long-term use. $5\text{-}HT_{1A}$ receptor partial agonists also have useful anxiolytic and other psychotropic activity, and less likelihood of sedation and dependance (see R. J. Baldessarini in *Goodman & Gilman's The Pharmacological Basis of Therapeutics*, 9th Edition, Chapter 18, McGraw-Hill, 1996 for a review).

Neurokinin 1 (NK-1; substance P) receptor antagonists are being developed for the treatment of a number of physiological disorders associated with an excess or imbalance of tachykinins, and in particular substance P. Examples of such conditions include disorders of the central nervous system such as anxiety, depression and psychosis (see, for instance, International (PCT) patent specification Nos. WO 95/16679, WO 95/18124 and WO 95/23798).

WO98/15277 teaches the use of a CNS-penetrant NK-1 receptor antagonist and a (separate) antidepressant or anti-anxiety agent for the treatment or prevention of depression and/or anxiety. Included among the classes of antidepressants and anti-anxiety agents disclosed as suitable for this use are selective serotonin reuptake inhibitors (SSRIs). However, there is neither disclosure nor suggestion of any compound fulfilling the dual roles of NK-1 receptor antagonist and SSRI.

WO94/10165 discloses certain 4-arylmethyloxymethyl piperidines as tachykinin antagonists. However, there is neither disclosure nor suggestion of any compound as claimed herein.

The compounds of the present invention are useful in the treatment of depression and/or anxiety by virtue of their activity as NK-1 receptor antagonists or their activity as selective serotonin re-uptake inhibitors. Advantageously a preferred class of compound of the present invention exhibit both NK-1 receptor antagonist and selective serotonin re-uptake inhibitor activity.

The present invention provides a compound of formula (I) or a pharmaceutically acceptable salt or a prodrug thereof:

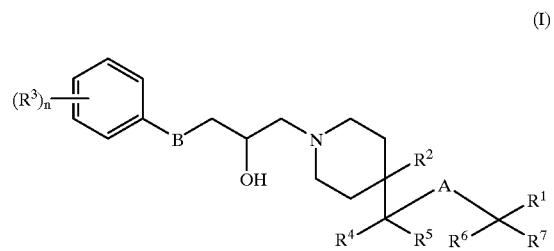

(I)

wherein $R^1$ and $R^2$ each independently represents a phenyl group optionally substituted by 1, 2 or 3 groups selected from $C_{1-6}$alkyl, $C_{2-6}$alkenyl, $C_{2-6}$alkynyl, cyclo$C_{3-7}$alkyl, cyclo$C_{3-7}$alkyl$C_{1-4}$alkyl, cyclo$C_{3-7}$alkoxy, fluoro$C_{1-6}$alkyl, $C_{1-6}$alkoxy, fluoro$C_{1-6}$alkoxy, hydroxy, phenoxy, halo, cyano, nitro, —$SR^a$, —$SOR^a$, —$SO_2R^a$, —$NR^aR^b$, —$NR^aCOR^b$, —$NR^aCO_2R^b$, —$COR^a$, —$CO_2R^a$ or —$CONR^aR^b$;

$R^3$ represents halogen, cyano, nitro, $C_{1-8}$alkyl, $C_{2-6}$alkenyl, $C_{2-6}$alkynyl, cyclo$C_{3-7}$alkyl, cyclo$C_{3-7}$alkyl$C_{1-4}$alkyl, cyclo$C_{3-7}$alkoxy, fluoro$C_{1-6}$alkyl, $C_{1-6}$alkoxy, fluoro$C_{1-6}$alkoxy, hydroxy, hydroxy$C_{1-6}$alkyl, hydroxy$C_{1-6}$alkoxy, —$SR^a$, —$SOR^a$, —$SO_2R^a$, —$NR^aR^b$, —$NR^aCOR^b$, —$NR^aCO_2R^b$, —$COR^a$, —$CO_2R^a$, —$CONR^aR^b$, adamantyl, morpholinyl (optionally substituted by one or two $C_{1-4}$alkyl groups), phenyl, phenoxy, phenylazo, benzyl or benzyloxy, wherein said phenyl or the phenyl moiety of said phenoxy, phenylazo or benzyloxy groups is optionally substituted by one or two substituents selected from halogen, $C_{1-4}$alkyl, $C_{1-4}$alkoxy or hydroxy; or, when n is 2, 3, 4 or 5 two groups $R^3$ on adjacent carbon atoms are linked by —$OCH_2O$—, —$OCH_2CH_2O$—, —$CH_2CH_2CH_2$—, —$CH_2CH=CH$—, —$NR^a$—$CH=CH$— or —$OC(R^a)_2CH_2C(O)$—;

$R^4$, $R^5$, $R^6$, and $R^7$ each independently represents hydrogen or $C_{1-6}$alkyl;

$R^a$ and $R^b$ each independently represents hydrogen, $C_{1-6}$alkyl, phenyl or trifluoromethyl;

A represents —O— or —S—;

B represents —O—, —S—, —$NR^a$— or —$CHR^a$—; and n is zero, 1, 2, 3, 4 or 5.

As used herein, the expression "$C_{1-8}$alkyl" includes methyl and ethyl groups, and straight-chained or branched propyl, butyl, pentyl, hexyl and octyl groups. Particular alkyl groups are methyl, ethyl, n-propyl, isopropyl and tert-butyl. Derived expressions such as "$C_{1-6}$alkoxy" are to be construed accordingly.

The expression "$C_{2-6}$alkenyl" as used herein refers to straight-chained and branched alkenyl groups containing from 2 to 6 carbon atoms. Typical examples include vinyl, allyl, dimethylallyl and butenyl groups.

The expression "$C_{2-6}$alkynyl" as used herein refers to straight-chained and branched alkynyl groups containing from 2 to 6 carbon atoms. Typical examples include ethynyl and propargyl groups.

As used herein, the term "fluoro$C_{1-6}$alkyl" and "fluoro$C_{1-6}$ alkoxy" means a $C_{1-6}$alkyl or $C_{1-6}$alkoxy group in which one or more (in particular, 1 to 3) hydrogen atoms have been replaced by fluorine atoms. Particularly preferred are fluoroC$_{1-3}$alkyl and fluoroC$_{1-3}$alkoxy groups, for example, CF$_3$, CH$_2$CH$_2$F, CH$_2$CHF$_2$, CH$_2$CF$_3$, OCF$_3$, OCH$_2$CH$_2$F, OCH$_2$CHF$_2$ or OCH$_2$CF$_3$, and most especially CF$_3$, OCF$_3$ and OCH$_2$CF$_3$.

As used herein, the term "hydroxyC$_{1-6}$alkyl" and "hydroxyC$_{1-6}$alkoxy" means a C$_{1-6}$alkyl or C$_{1-6}$alkoxy group substituted at any substitutable position by a hydroxy group. Particularly preferred are hydroxyC$_{1-2}$alkyl and hydroxyC$_{2-3}$alkoxy groups, for example, CH$_2$OH, CH$_2$CH$_2$OH, OCH$_2$CH$_2$OH or O(CH$_2$)$_3$OH, and most especially OCH$_2$CH$_2$OH.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy. A suitably cycloalkylalkoxy group may be, for example, cyclopropylmethoxy.

The term "halogen" as used herein includes fluorine, chlorine, bromine and iodine, especially fluorine.

It will be appreciated that where n is 2, 3, 4 or 5, each substituent R$^3$ may be the same or different.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in *Design of Prodrugs*, ed. H. Bundgaard, Elsevier, 1985.

Certain compounds according to the present invention may be capable of existing as tautomeric forms. It is to be understood that all possible tautomers and mixtures thereof in any proportion are encompassed within the scope of the present invention.

The compounds according to the invention have at least one asymmetric centre, and may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula (I), —O— and —S— are suitable identities for A, but —O— is preferred.

Particular identities for B include —O—, —S—, —NH—, —NCH$_3$— and —CH$_2$—, but —O— is preferred.

R$^4$, R$^5$, R$^6$ and R$^7$ each independently represents hydrogen or C$_{1-6}$alkyl, but preferably each of R$^4$, R$^5$, R$^6$ and R$^7$ represents hydrogen.

Hence, a preferred class of compounds are the compounds of formula (IA), or a pharmaceutically acceptable salt or prodrug thereof:

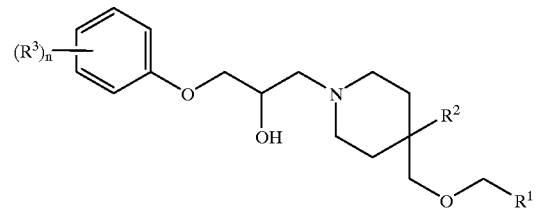

(IA)

wherein R$^1$, R$^2$, R$^3$ and n are as defined for formula (I).

R$^1$ in formula (I) and formula (IA) represents phenyl or substituted phenyl, but preferably R$^1$ represents substituted phenyl. When R$^1$ is substituted phenyl, suitable substituents include nitro, trifluoromethyl, bromo, chloro, fluoro, iodo, cyano, methyl, ethyl, cyclopropyl, tert-butyl, vinyl, methoxy, phenoxy, and amino. Preferably R$^1$ represents phenyl substituted by one or more groups selected from C$_{1-6}$alkyl such as methyl and tert-butyl, halo such as chloro, fluoro and bromo, and trifluoromethyl.

Preferably R$^1$ represents disubstituted phenyl, in particular 3,5-disubstituted phenyl, for example 3,5-disubstituted phenyl wherein the substituents are selected from C$_{1-6}$alkyl, halo and trifluoromethyl. More preferably R$^1$ represents 3,5-bis(trifluoromethyl)phenyl.

R$^2$ in formula (I) and formula (IA) represents phenyl or substituted phenyl, but preferably R$^2$ represents unsubstituted phenyl. When R$^2$ represents substituted phenyl, any of the substituents listed in connection with R$^1$ may be present, but a preferred substituent is halo, especially fluoro.

Hence, a further preferred class of compounds are the compounds of formula (IB), or a pharmaceutically acceptable salt or prodrug thereof:

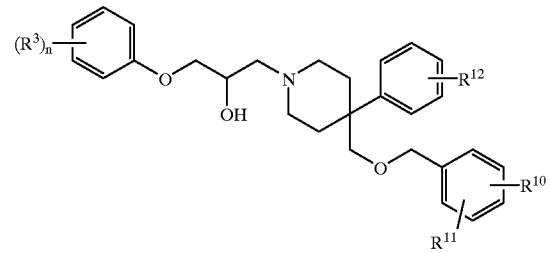

(IB)

wherein

R³ and n are as defined for formula (I);

R¹⁰ and R¹¹ each independently represent hydrogen, halogen, $C_{1-6}$alkyl or trifluoromethyl; and R¹² represents hydrogen or halogen.

Particular values of R¹⁰ and R¹¹ include hydrogen, chlorine, bromine, methyl, tert-butyl and trifluoromethyl. Preferably, R¹⁰ and R¹¹ are both other than hydrogen and are located at the 3- and 5-positions on the phenyl ring.

Particular values of R¹² are hydrogen and fluorine. Where R¹² is other than hydrogen, the group is preferably located at the 4-position of the phenyl ring.

R³ in formula (I), formula (IA) and formula (IB) is preferably selected from halogen, cyano, nitro, $C_{1-8}$alkyl, $C_{2-4}$alkenyl, fluoro$C_{1-3}$alkyl, fluoro$C_{1-3}$alkoxy, $C_{1-6}$alkoxy, hydroxy$C_{2-3}$alkoxy, NR$^a$COR$^b$, —CO₂R$^a$, adamantyl, 2,6-dimethylmorpholino, phenyl, phenoxy, phenylazo or benzyloxy, wherein said phenyl group or the phenyl moiety of said phenoxy, phenylazo, or benzyloxy group is unsubstituted or substituted by $C_{1-4}$alkyl, or when n is 2, 3, 4 or 5, two groups R³ on adjacent carbon atoms are linked by —OCH₂O—, —CH₂CH₂CH₂—, —NHCH=CH— or —OC(CH₃)₂CH₂C(O)—.

Hence, a further preferred class of compound of formula (I), formula (IA) and formula (IB) is that wherein n is 1 or 2 and R³ is selected from fluoro, chloro, cyano, methyl, methoxy, —OCH₂CH₂OH or —NHCOCH₃ or n is 3 wherein two groups R³ on adjacent carbon atoms are linked by —CH₂CH₂CH₂— and the other group R³ is bromine, or n is 5 and R³ is selected from fluoro and trifluoromethyl.

Another preferred class of compound of formula (I), formula (IA) and formula (IB) is that wherein n is zero or 1 and R³ is selected from fluoro, ethyl, phenyl, phenoxy or 2,6-dimethylmorpholino, or n is 2 and R³ is selected from fluoro, methoxy and cyano, or n is 3 wherein two groups R³ on adjacent carbon atoms are linked by —OC(CH₃)₂CH₂C(O)— and the other group R³ is chloro.

A further preferred class of compound of formula (I), formula (IA) and formula (IB) is that wherein n is 1 or 2 and R³ is selected from chloro, bromo, methyl, t-butyl, allyl, adamantyl, cumyl or two groups R³ on adjacent carbon atoms are linked by —OCH₂O—.

Specific compounds within the scope of this invention include:

3-(3-acetamidophenyloxy)-1-[4-phenyl-4-[3,5-bis (trifluoromethyl)benzyloxymethyl]piperidine]-propan-2-ol;

3-(3-phenyloxy)-1-[4-phenyl-4-[3,5-bis(trifluoromethyl) benzyloxymethyl]piperidine]-propan-2-ol;

3-(3,5-dimethylphenyloxy)-1-[4-phenyl-4-[3,5-bis (trifluoromethyl)benzyloxymethyl]piperidine]-propan-2-ol;

3-(4-methoxyphenyloxy)-1-[4-phenyl-4-[3,5-bis (trifluoromethyl)benzyloxymethyl]piperidine]-propan-2-ol;

3-(4-chlorophenyloxy)-1-[4-phenyl-4-[3,5-bis (trifluoromethyl)benzyloxymethyl]piperidine]-propan-2-ol;

3-(3,4-dimethylphenyloxy)-1-[4-phenyl-4-[3,5-bis (trifluoromethyl)benzyloxymethyl]piperidine]-propan-2-ol;

3-(4-fluorophenyloxy)-1-[4-phenyl-4-[3,5-bis (trifluoromethyl)benzyloxymethyl]piperidine]-propan-2-ol;

3-(3-ethylphenyloxy)-1-[4-phenyl-4-[3,5-bis (trifluoromethyl)benzyloxymethyl]piperidine]-propan-2-ol;

3-(2-cyanophenyloxy)-1-[4-phenyl-4-[3,5-bis (trifluoromethyl)benzyloxymethyl]piperidine]-propan-2-ol;

1-[4-phenyl-4-[3,5-bis(trifluoromethyl) benzyloxymethyl]piperidine]-3-(4-trifluoromethoxyphenyloxy)-propan-2-ol;

and pharmaceutically acceptable salts thereof.

The invention also provides pharmaceutical compositions comprising one or more compounds of this invention in association with a pharmaceutically acceptable carrier.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides a process for the preparation of a pharmaceutical composition comprising a compound of formula (I), which process comprises bringing a compound of formula (I) into association with a pharmaceutically acceptable carrier or excipient.

By virtue of their activity as tachykinin (especially neurokinin-1 receptor) antagonists, the compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and anmestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, bronchospasm and cough; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or domperidone or GABA$_B$ receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and headache, including migraine, acute or chronic tension headache, cluster headache; temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or depression.

The present invention further provides a compound of formula (1) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination.

Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

By virtue of their dual efficacy as tachykinin (especially neurokinin-1 receptor) antagonists and serotonin reuptake inhibitors, the compounds of the present invention are especially useful for the treatment of depression. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

By virtue of their dual efficacy as tachykinin (especially neurokinin-1 receptor) antagonists and serotonin reuptake inhibitors, the compounds of the present invention are also especially useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

"Generalised anxiety" is typically defined as an extended period (e.g. at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterised by an anxiety about being in places or situations from which escape might be difficult or embarrassing or in which help may not be available in the event of a panic attack. Agoraphobia may occur without history of a panic attack. A "specific phobia" is characterised by clinically significant anxiety provoked by exposure to a specific feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or otherwise invasive medical procedure; situational type, cued by a specific situation such as public transportation, tunnels, bridges, elevators, flying, driving or enclosed spaces; and other type where fear is cued by other stimuli. Specific phobias may also be referred to a simple phobias. A "social phobia" is characterised by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencyclidine, sedatives, hypnotics, anxiolytics and other substances, and adjustment disorders with anxiety or with mixed anxiety and depression.

Anxiety may be present with or without other disorders such as depression in mixed anxiety and depressive disorders. The compositions of the present invention are therefore useful in the treatment of anxiety with or without accompanying depression.

The compounds of the present invention are especially useful for the treatment of or prevention of depression and/or anxiety where the use of an antidepressant or anti-anxiety agent is generally prescribed. By the use of a compound in accordance with the present invention, it is now also possible to treat or prevent depression and/or anxiety in patients for whom conventional antidepressant or anti-anxiety therapy might not be wholly successful or where dependence upon the antidepressant or anti-anxiety therapy is prevalent.

According to a further or alternative aspect, the present invention provides a compound of formula (I) or a pharmaceutically acceptable salt or prodrug thereof for use in the manufacture of a medicament for the treatment or prevention of depression and/or anxiety.

The present invention also provides a method for the treatment or prevention of depression and/or anxiety, which method comprises administration to a patient in need of such treatment a therapeutically effective amount of a compound of formula (I) or a pharmaceutically acceptable salt or prodrug thereof.

By combining NK-1 receptor antagonist activity with SSRI activity, the compounds of the invention show therapeutic effects in the treatment or prevention of depression and/or anxiety previously obtainable only by the administration of two separate compounds, as described in WO98/15277. The use of a single compound simplifies the manufacture of the relevant pharmaceutical compositions, and obviates any need on the part of health care professionals to prescribe or administer separate compositions.

It will be appreciated, however, that in certain circumstances, it may also be desirable to use a compound of the present invention in conjunction with other anti-depressant or anti-anxiety agents for the treatment of depression and/or anxiety.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal, especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

A further aspect of the present invention comprises the use of a compound of formula (I) for achieving a chronobiologic (circadian rhythm phase-shifting) effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The compounds of the present invention are also of use in the treatment or prevention of mania, including hypomania.

The present invention accordingly provides the use of a compound of formula (I) for the manufacture of a medicament for the treatment or prevention of mania, including hypomania.

The present invention also provides a method for the treatment or prevention of mania, including hypomania, which method comprises administration to a patient in need of such treatment of an -effective amount of a compound of formula (I).

In a further aspect of the present invention, there is provided a pharmaceutical composition for the treatment or prevention of mania, including hypomania, comprising a compound of formula (I), together with at least one pharmaceutically acceptable carrier or excipient.

It will be appreciated that a combination of a conventional antipsychotic drug with a compound of formula (I) may provide an enhanced effect in the treatment of mania, including hypomania.

Thus, according to a further aspect of the present invention there is provided the use of a compound of formula (I) and an antipsychotic agent for the manufacture of a medicament for the treatment or prevention of mania, including hypomania.

The present invention also provides a method for the treatment or prevention of mania, including hypomania, which method comprises administration to a patient in need of such treatment of an amount of a compound of formula (I) and an amount of an antipsychotic agent, such that together they give effective relief.

In a further aspect of the present invention, there is provided a pharmaceutical composition comprising a compound of formula (I) and an antipsychotic agent, together with at least one pharmaceutically acceptable carrier or excipient.

It will be appreciated that the compound of formula (I) and the antipsychotic agent may be present as a combined preparation for simultaneous, separate or sequential use for the treatment or prevention of mania, including hypomania. Such combined preparations may be, for example, in the form of a twin pack.

In a further or alternative aspect of the present invention, there is therefore provided a product comprising a compound of formula (I) and an antipsychotic agent as a combined preparation for simultaneous, separate or sequential use in the treatment or prevention of mania, including hypomania.

The compounds of the present invention are also of use in the treatment or prevention of aggressive behaviour disorders.

The present invention accordingly provides the use of a compound of formula (I) for the manufacture of a medicament for the treatment or prevention of aggressive behaviour.

The present invention also provides a method for the treatment or prevention of aggressive behaviour, which method comprises administration to a patient in need of such treatment of an effective amount of a compound of formula (I).

In a further aspect of the present invention, there is provided a pharmaceutical composition for the treatment or prevention of aggressive behaviour comprising a compound of formula (I), together with at least one pharmaceutically acceptable carrier or excipient.

It will be appreciated that a combination of a conventional antipsychotic drug with a compound of formula (I) may provide an enhanced effect in the treatment of aggressive behaviour.

Thus, according to a further aspect of the present invention there is provided the use of a compound of formula (I) and an antipsychotic agent for the manufacture of a medicament for the treatment or prevention of aggressive behaviour.

The present invention also provides a method for the treatment or prevention of aggressive behaviour, which method comprises administration to a patient in need of such treatment of an amount of a compound of formula (I) and an amount of an antipsychotic agent, such that together they give effective relief.

It will be appreciated that the compound of formula (I) and the antipsychotic agent may be present as a combined preparation for simultaneous, separate or sequential use for the treatment or prevention of aggressive behaviour. Such combined preparations may be, for example, in the form of a twin pack.

In a further or alternative aspect of the present invention, there is therefore provided a product comprising a compound of formula (I) and an antipsychotic agent as a combined preparation for simultaneous, separate or sequential use in the treatment or prevention of aggressive behaviour.

As used herein, the term "aggressive behaviour" includes explosive personality disorder, intermittent explosive disorder, aggressive personality, aggressive nature, aggressiveness, excessive emotional instability, pathological emotionality, quarrelsomeness, dementia with behavioural disturbance, and personality change of the aggressive type due to a general medical condition.

Aggressive behaviour may also be associated with substance intoxication, substance withdrawal, oppositional defiant disorder, conduct disorder, antisocial personality disorder, borderline personality disorder, a manic episode and schizophrenia.

Suitable antipsychotic agents of use in combination with a compound of formula (I) include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a compound of formula (I) may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

In the treatment of depression and/or anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day, or more preferably once or twice daily.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The present invention further provides a compound of formula (I) or a pharmaceutically acceptable salt or prodrug thereof for use in therapy.

The compounds of formula (I) may be prepared by reaction of an epoxide of formula (II) with a piperidine of formula (III):

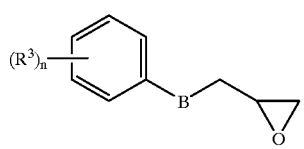
(II)

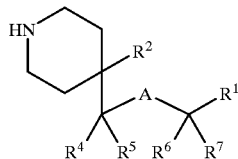

wherein A, B, $R^1$, $R^2$, $R^3$, $R^4$, $R^5$, $R^6$, $R^7$ and n are as previously defined.

The reaction is typically carried out by heating approximately equimolar quantitities of the reagents in an inert solvent (such as acetonitrile) at moderately elevated temperatures for an appropriate length of time (typically about 18 hours). The piperidines of formula (III) may be prepared by the methods disclosed in WO94/10165.

The epoxides of Formula (II) in which B is other than —$CHR^a$— may be prepared by reacting a compound of formula (IV) with a compound of formula (V) in the presence of base:

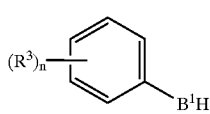
(IV)

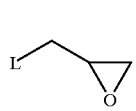
(V)

wherein $R^3$ and n are as previously defined, $B^1$ represents —O—, —S— or —$NR^a$—, and L represents a leaving group, such as an alkyl- or arylsulfonyloxy group (e.g. mesylate or tosylate) or a halogen atom (e.g. bromine, chlorine, or iodine) or a 3-nitrophenoxy group.

Suitable bases of use in this reaction include alkali metal carbonates, such as potassium carbonate.

In an alternative method of preparation, compounds of formula (I) in which B is other than —$CHR^a$— may be obtained by reaction of a compound of formula (IV) with a compound of formula (VI) in the presence of base:

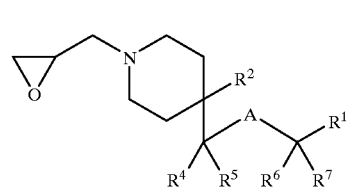
(VI)

wherein A, $R^1$, $R^2$, $R^4$, $R^5$, $R^6$ and $R^7$ are as previously defined. The compounds of formula (VI) may be obtained by reaction of a compound of formula (III) with a compound of formula (V) in the presence of base.

Compounds of formula (I) in which B represents —$CHR^a$— may be prepared by reacting a compound of formula (VI) with a compound of formula (VII):

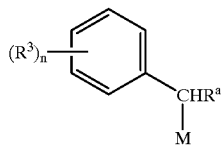 (VII)

wherein $R^3$, n and $R^a$ are as previously defined, and M represents Li or MgHal where Hal represents chlorine, bromine or iodine.

Where they are not commercially available, the starting materials of formulae (IV), (V) and (VII) may be prepared by methods analogous to those described in the accompanying Examples, or by standard procedures well known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

The compound of formula (V) in which L is chlorine is readily available in optically pure (+) and (−) forms, which represent convenient starting materials for enantiospecific synthesis at compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

It will be understood that any compound of formula (I) initially obtained from any of the above processes may, where appropriate, subsequently be elaborated into a further compound of formula (I) by techniques known from the art. For example, a compound of formula (I) in which $R^1$ or $R^2$ bears a nitro substituent, may be subjected to catalytic hydrogenation to form the corresponding primary amine, which in turn may be alkylated by standard methods (such as reductive alkylation by an aldehyde or ketone in the presence of sodium cyanoborohydride), or acylated by reaction with an acyl chloride, or carbamoylated by reaction with an alkyl chloroformate. Similarly, a compound of formula (I) in which $R^1$ or $R^2$ bears an alkoxycarbonyl substituent, or in which $R^3$ represents an alkoxycarbonyl group, may be transesterified by treatment with the appropriate alcohol in the presence of a mineral acid such as sulfuric acid, or saponified by treatment with alkali metal hydroxide to the corresponding carboxylic acid, which in turn may be converted to an amide by treatment with the appropriate amine, advantageously in the presence of 1-(3-dimethylaminopropyl)-3-ethylcarbodiimide hydrochloride and 1-hydroxybenzotriazole. Moreover, a compound of formula (I) in which $R^1$ or $R^2$ is substituted by $C_{1-6}$alkoxy, may be converted to the corresponding phenol by treatment with boron tribromide, typically in dichloromethane.

The compounds in accordance with the invention combine NK-1 receptor antagonist activity with SSRI activity. As NK-1 receptor antagonists, the compounds of the invention typically have an NK-1 receptor affinity ($IC_{50}$) of less than 100 nM, and preferably less than 10 nM.

NK-1 receptor binding assays are well known in the art. The following assay is one such protocol based upon the displacement of $^{125}$I-Tyr$^8$-substance P binding to cloned human NK-1 receptors in vitro:

ASSAY 1: NK-1 Receptor Binding Assay

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. Typically, the receptor is expressed at a level of $3 \times 10^5$ receptors per cell. Cells are grown in monolayer culture, detached from the plate with enzyme-free dissociation solution (Speciality Media Inc.), and washed prior to use in the assay. $^{125}$I-Tyr$^8$-substance P (0.1 nM, 2000 Ci/mmol; New England Nuclear) is incubated in the presence or absence of test compounds (dissolved in 5 μl dimethylsulphoxide, DMSO) with $5 \times 10^4$ CHO cells. Ligand binding is performed in 0.25 ml of 50 mM Tris-HCl, pH7.5, containing 5 mM $MnCl_2$, 150 mM NaCl, 0.02% bovine serum albumin (Sigma), 50 μg/ml chymostatin (Peninsula), 0.1 nM phenylmethylsulphonyl fluoride, 2 μg/ml pepstatin, 2 μg/ml leupeptin and 2.8 μg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 μM) and represents <10% of total binding.

ASSAY 2: Human 5-HT Transporter Binding Assay

Human 5-HT transporter binding assays may be performed by a variety of techniques well known in the art, for example, using the assay conditions described in *Biochemical Pharmacology* (1996) 51:1145–1151 or a modification thereof A typical method is as follows:

Membrane Preparation

1. On the day of the assay, HEK cells expressing the h5-HT transporter are homogenised in ice cold wash buffer using a Kinematic polytron and centrifuged at 45,000×g (19,500 rpm) for 10 minutes at 4° C.

2. The resulting supernatant is discarded and the pellet is weighed, re-homogenised and centrifuged as above before being resuspended in assay buffer to give 0.3 mg washed wet weight/well.

Radioligand Binding Assay

3. Binding is determined using 5 nM [$^3$H]citalopram (Net 1039, specific activity 70–87 Ci/mmol; NEN Products), made up in assay buffer.

4. Non-specific binding is determined using 0.5 μM paroxetine.

5. 50 μl unknown drug is added to a final volume of 0.5 ml.

6. The incubation wells are set up as follows:

|  | Paroxetine | Drug | Ligand | Buffer | Membrane |
|---|---|---|---|---|---|
| TOTAL |  |  | 50 μl | 350 μl | 100 μl |
| NON-SPECIFIC | 50 μl |  | 50 μl | 300 μl | 100 μl |
| DRUG |  | 50 μl | 50 μl | 300 μl | 100 μl |

7. The assay is initiated by the addition of 100 μl of membrane suspension.
8. The plates are incubated at room temperature for 60 minutes.
9. The assay is terminated by filtering, followed by 3×1 ml wash with ice cold wash buffer.
10. The filters are left to dry for 30 minutes and counted.
Assay/Wash Buffer
50 mM Tris (30.3 g/5 L)
120 mM NaCl (35.05 g/5 L) pH 7.4 at room temperature, using HCl
5 mM KCl (1.85 g/5 L)

Pharmacological assays for the study of antidepressant or anti-anxiety activity are well known in the art. Many are based upon the ability of antidepressants to support animal behaviour in stressful situations that ordinarily lead to diminished behavioural responsiveness ("learned helplessness"), such as repeated noxious shocks, forced swimming, or separation from other animals.

The following non-limiting Examples serve to illustrate the preparation of compounds of the present invention:

Description 1

Representative Experimental Conditions: Glass tubes (12 mm diameter) were charged with substituted phenol (2 mmol), potassium carbonate (4 mmol) and epichlorohydrin (6 mmol). The contents were mixed by vortex before the tubes were flushed with nitrogen, sealed and heated at 50° C. in a heating block for 18 hours. Acetonitrile (3 ml) was added and the contents mixed. Solid was removed by filtration of individual tubes through a fritted, disposable syringe. Concentration of the filtrate gave the required epoxides together with the corresponding chloro alcohols. These were stored at −78° C. until required. Glass tubes were charged with epoxide (64 μM), amine (49 μM) and acetonitrile (1 ml). The tubes were flushed with nitrogen, sealed and heated at 50° C. in a heating block for 18 hours. The tubes were allowed to cool and methanol (1 ml) was added to solubilise the contents which were applied to a 5 ml disposable syringe containing Amberlyst™ 15 resin (4 ml). The contents were allowed to stand for 10 minutes before being collected as waste. The Amberlyst™ 15 resin was washed successively with a syringe volume of acetonitrile-water (1:1), acetonitrile (2 times), acetonitrile-$NH_4OH$ (4% solution). These washings were discarded. The washings from acetonitrile-$NH_4OH$ (10% then 20% solutions) were collected in pre-weighed tubes and concentrated prior to analysis by mass spectral analysis.

The following were prepared using this procedure:

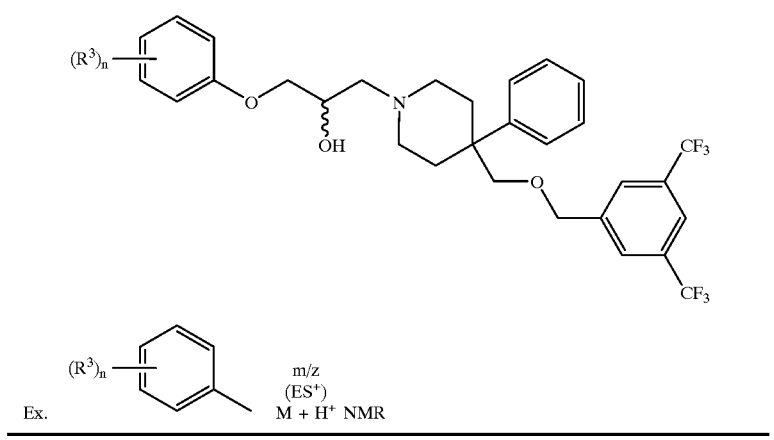

| Ex. | $(R^3)_n$-phenyl | m/z (ES+) M + H+ | NMR |
|---|---|---|---|
| 1 | 3,5-dipropoxyphenyl | 684 |  |
| 2 | 2,4,5-trichlorophenyl | 671 |  |
| 3 | 3-acetamidophenyl | 625 | $\delta_H$ (360 MHz, DMSO-$d_6$) 2.02 (3H, s) 2.03–2.47 (4H, m), 3.00–3.28 (4H, m), 3.35–3.58 (4H, m), 3.87 (2H, m, $OCH_2$), 4.26 (1H, m), 4.58 (2H, s, $OCH_2$), 6.61 (1H, m, ArH), 7.01 (1H, m, ArH), 7.18 (1H, m, ArH), 7.30 (1H, m, ArH), 7.36–7.50 (5H, m, ArH), 7.76 (2H, s, ArH), 7.98 (1H, s, ArH), 9.92 (1H, br s, NH) |
| 4 | 3,4-methylenedioxyphenyl | 612 |  |
| 5 | 3,5-bis(methylcarboxylate)-phenyl | 684 |  |
| 6 | 2,3,5,6-tetrafluoro-4-trifluoromethylphenyl | 708 |  |
| 7 | 4-butoxyphenyl | 640 |  |

-continued

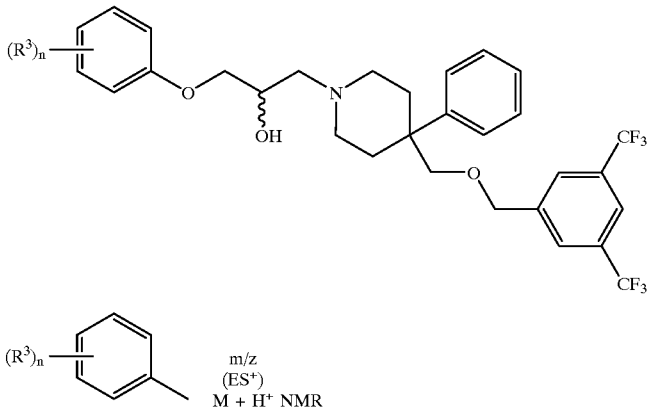

| Ex. | (R³)ₙ—[phenyl] | m/z (ES⁺) M + H⁺ | NMR |
|---|---|---|---|
| 8 *1 | phenyl | 568 | $\delta_H$(360 MHz, CDCl₃) 2.02 (2H, s), 2.29 (3H, m), 2.50 (4H, m), 2.80 (1H, m), 3.48 (2H, m, OCH₂), 3.96 (2H, m), 4.06 (1H, m), 4.43 (2H, s, OCH₂), 6.92 (3H, m, ArH), 7.31 (7H, m, ArH), 7.54 (2H, s, ArH), 7.74 (1H, s, ArH) |
| 8 *2 | phenyl | 568 | $\delta_H$ (360 MHz, DMSO-d₆) 2.06–2.52 (4H, m), 2.60–3.10 (4H, m), 3.30–3.40 (2H, m), 3.45–3.58 (2H, m), 3.90 (2H, m, OCH₂), 4.23 (1H, m), 4.57 (2H, m, OCH₂), 6.92–6.97 (3H, m, ArH), 7.27–7.47 (7H, m, ArH), 7.76 (2H, s, ArH), 7.98 (1H, s, ArH) |
| 8 *3 | phenyl | 568 | $\delta_H$ (360 MHz, DMSO-d₆) 2.06–2.48 (4H, m), 2.60–3.10 (4H, m), 3.30–3.60 (4H, m), 3.80–3.90 (2H, m, OCH₂), 4.26 (1H, m), 4.57 (2H, m, OCH₂), 6.92–6.97 (3H, m, ArH), 7.27–7.47 (7H, m, ArH), 7.76 (2H, s, ArH), 7.98 (1H, s, ArH) |
| 9 | 4-phenylazophenyl | 672 | |
| 10 | 5-(2,3-benzopyrrole) | 608 | |
| 11 | 3-chloro-5-methoxy-phenyl | 633 | |
| 12 | 3-fluoro-4-cyano-phenyl | 611 | |
| 13 | 4-(t-octyl)phenyl | 680 | |
| 14 | 4-cyano-3-methoxy-phenyl | 623 | |
| 15 | 2-t-butylphenyl | 624 | |
| 16 | 3-t-butylphenyl | 624 | |
| 17 | 4-t-butylphenyl | 624 | |
| 18 | 4-acetamidophenyl (thio ether linker - i.e. B = S) | 641 | |
| 19 | 2-bromo-4-chloro-phenyl | 681 | |
| 20 | 4-bromophenyl | 647 | |
| 21 | 2-bromo-5-fluoro-phenyl | 665 | |
| 22 | 2-bromo-4,5-difluorophenyl | 683 | |
| 23 | 2-bromophenyl | 647 | |
| 24 | 2-bromo-4-methyl-phenyl | 661 | |
| 25 | 2-bromo-4-fluorophenyl | 665 | |
| 26 | 2-benzyloxyphenyl | 674 | |
| 27 | 2-allylphenyl | 608 | |
| 28 | 4-bromo-2-methyl-phenyl | 661 | |
| 29 | 4-benzyloxyphenyl | 674 | |
| 30 | 3-chloro-4-fluorophenyl | 620 | |
| 31 | 3,5-dimethylphenyl | 596 | $\delta_H$ (360 MHz, CDCl₃) 2.04 (2H, m), 2.28 (9H, m), 2.49 (3H, m), 2.62 (1H, m), 2.84 (1H, m), 3.47 (2H, s, OCH₂), 3.92 (2H, m), 4.07 (1H, m), 4.43 (2H, s, OCH₂), 6.56 (3H, m, ArH), 7.26 (1H, m, ArH), 7.37 (4H, m, ArH), 7.54 (2H, s, ArH), 7.74 (1H, s, ArH) |
| 32 | 4-chloro-3-methyl-phenyl | 616 | |
| 33 | 4-methoxyphenyl | 598 | $\delta_H$ (360 MHz, DMSO-d₆) 2.08–2.45 (4H, m), 2.99–3.21 (4H, m), 3.35–3.58 (4H, m), 3.69 (3H, s, OCH₃), 3.84 (2H, m, OCH₂), 4.20 (1H, m), 4.57 (2H, s, OCH₂), 6.86 (4H, m, ArH), 7.28–7.46 (5H, m, ArH), 7.76 (2H, s, ArH), 7.97 (1H, s, ArH) |

-continued

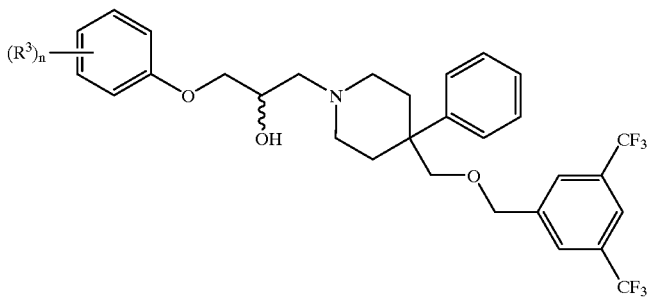

| Ex. | 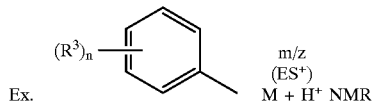 (R³)ₙ | m/z (ES⁺) M + H⁺ | NMR |
|---|---|---|---|
| 34 | 2-(2-hydroxyethoxy)-phenyl | 628 | |
| 35 | 3-methoxyphenyl | 598 | |
| 36 | 2,5-dichlorophenyl | 637 | |
| 37 | 3-chlorophenyl | 602 | |
| 38 | 4-chlorophenyl | 602 | $\delta_H$ (360 MHz, CDCl₃) 2.00 (2H, m), 2.26 (3H, m), 2.44 (4H, m), 2.82 (1H, m), 3.47 (2H, s, OCH₂), 3.91 (2H, m), 4.06 (1H, m), 4.43 (2H, s, OCH₂), 6.84 (3H, m, ArH), 7.20–7.37 (6H, m, ArH), 7.54 (2H, s, ArH), 7.74 (1H, s, ArH) |
| 39 | 2,4-dichlorophenyl | 637 | |
| 40 | 3,5-dimethoxyphenyl | 628 | |
| 41 | 2-chlorophenyl | 602 | |
| 42 | 3,4-dibenzyloxyphenyl | 780 | |
| 43 | 3,4-dichlorophenyl | 637 | |
| 44 | 3,4-dimethylphenyl | 596 | $\delta_H$ (360 MHz, CDCl₃) 1.96–2.08 (2H, m), 2.18–2.24 (9H, m), 2.43–2.51 (3H, m), 2.62 (1H, m), 2.82 (1H, m), 3.47 (2H, s, OCH₂), 3.91 (2H, m), 4.05 (1H, m), 4.43 (2H, s, OCH₂), 6.64 (1H, m, ArH), 6.71 (1H, m, ArH), 7.00 (1H, m, ArH), 7.26 (1H, m, ArH), 7.36 (4H, m, ArH), 7.54 (2H, s, ArH), 7.73 (1H, s, ArH) |
| 45 | 2,3-dimethylphenyl | 596 | |
| 46 | 2,6-dichlorophenyl | 637 | |
| 47 | 2,4-dichlorophenyl | 637 | |
| 48 | 4-cumyl | 686 | |
| 49 | 4-fluorophenyl | 586 | $\delta_H$ (360 MHz, DMSO-d₆) 2.02–2.44 (4H, m), 2.78–3.18 (4H, m), 3.35 (2H, m), 3.54 (2H, m), 3.89 (2H, d, OCH₂), 4.22 (1H, m), 4.57 (2H, s, OCH₂), 6.94 (1H, t, ArH), 7.09–7.46 (8H, m, ArH), 7.75 (2H, s, ArH), 7.97 (1H, s, ArH) |
| 50 | 4-fluoro-2-methylphenyl | 600 | |
| 51 | 4-cyanophenyl | 593 | |
| 52 | 3,4-dimethoxyphenyl | 628 | |
| 53 | 3-cyanophenyl | 593 | |
| 54 | 2,3-dimethoxyphenyl | 628 | |
| 55 | 3,4-difluorophenyl | 604 | |
| 56 | 2,4-difluorophenyl | 604 | |
| 57 | 3-ethylphenyl | 596 | $\delta_H$ (360 MHz, DMSO-d₆) 1.16 (3H, t), 2.13–2.38 (4H, m), 2.56 (2H, q), 2.89–3.20 (4H, m), 3.52 (4H, br s), 3.89 (2H, d, OCH₂), 4.21 (1H, m), 3.89 (2H, d, OCH₂), 4.21 (1H, m), 4.57 (2H, s, OCH₂), 6.72–6.80 (3H, m, ArH), 7.18 (1H, m, ArH), 7.27 (1H, m), 7.35–7.46 (4H, m, ArH), 7.76 (2H, s, ArH), 7.97 (1H, s, ArH) |
| 58 | 2-ethylphenyl | 596 | |
| 59 | 2,3-dichlorophenyl | 637 | |
| 60 | 2-fluorophenyl | 586 | |
| 61 | 3-fluorophenyl | 586 | |
| 62 | 2-cyanophenyl | 593 | $\delta_H$ (360 MHz, DMSO-d₆) 2.38 (4H, m), 3.17 (4H, m), 3.47 (4H, m), 4.12 (2H, br s, OCH₂), 4.31 (1H, m), 4.58 (2H, br s, OCH₂), 7.11 (1H, t, ArH), 7.36 (6H, m, ArH), 7.70 (4H, m, ArH), 7.97 (1H, s, ArH) |
| 63 | 4-cyanophenyl | 593 | |
| 64 | 3-phenylphenyl | 644 | |
| 65 | 4-phenylphenyl | 644 | |
| 66 | 2-phenylphenyl | 644 | |

-continued

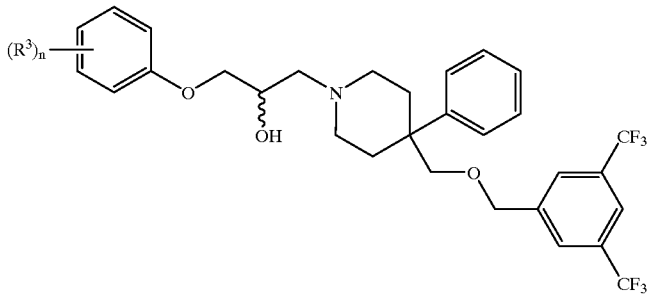

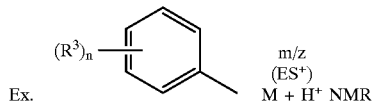

| Ex. | (R³)ₙ—[phenyl] | m/z (ES⁺) M + H⁺ | NMR |
|---|---|---|---|
| 67 | 4-trifluoromethoxyphenyl | 652 | δ_H (360 MHz, CDCl₃) 2.00 (2H, m), 2.27 (3H, m), 2.46 (3H, m), 2.62 (1H, m), 2.82 (1H, m), 3.47 (2H, s, OCH₂), 3.94 (2H, m), 4.07 (1H, m), 4.43 (2H, s, OCH₂), 6.90 (3H, m, ArH), 7.12 (1H, m, ArH), 7.26 (1H, m, ArH), 7.37 (4H, m, ArH), 7.55 (2H, s, ArH), 7.74 (1H, s, ArH) |
| 68 | 4-phenoxyphenyl | 660 | |
| 69 | 2-(2,6-dimethyl)-morpholinophenyl | 681 | |
| 70 | 7-(2,2-dimethyl-6-chloro-4-chromanone | 700 | |
| 71 | 4-(5-bromo-7-methyl-indane) | 700 | |
| 72 | 4-adamantyl-2-methylphenyl | 716 | |
| 73 | 2-ethyl-5-(3-methyl)butoxyphenyl | 696 | |

With reference to Example 8,
*1 = racemate
*2 = R-enantiomer
*3 = S-enantiomer

The examples shown above which have ¹H NMR data were re-synthesised in a similar manner as described below.

Description 2
3-ethylphenyloxy-1-[4-phenyl-4-[3,5-bis(trifluoromethyl)benzyloxymethyl]piperidine]-propan-2-ol oxalate (a) 3-ethylphenoxyoxirane To a stirred solution of 3-ethyl phenol (1.50 g, 12.28 mmol) in NaOH (1N) was added epichlorohydrin (2.07 g, 22.47 mmol). The reaction mixture was stirred at room temperature for 4 days. Excess epichlorohydrin was removed by concentration in vacuo and the two-phase mixture treated with NaOH (1N) (10 ml) after addition of THF (10 ml). The reaction mixture was heated to 55° C. for 15 minutes and then stirred at room temperature for 30 minutes. The THF was removed by concentration in vacuo and the product extracted with ethyl acetate (2×50 ml), concentrated in vacuo and purified by flash column chromatography on silica (150:10:1 dichloromethane:methanol:ammonia) to give the product as a yellow oil.

(b) 3-ethylphenyloxy-1-[4-phenyl-4-[3,5-bis(trifluoromethyl)-benzyloxymethyl]piperidine]-propan-2-ol oxalate The product from step (a) (200 mg, 1.12 mmol) was dissolved in isopropyl alcohol (10 ml) and refluxed with 4-phenyl-4-[3,5-(bistrifluoromethyl)-benzyloxymethyl]piperidine (375 mg, 0.90 mmol) for 16 hours. The reaction mixture was then concentrated in vacuo to give a yellow oil which was purified by flash column chromatography on silica (150:10:1 dichloromethane:methanol:ammonia) to give the title compound as a yellow oil. The salt was prepared by dissolving the product in diethyl ether and adding 1 equivalent of oxalic acid.

What we claim is:

1. A compound of the formula (I):

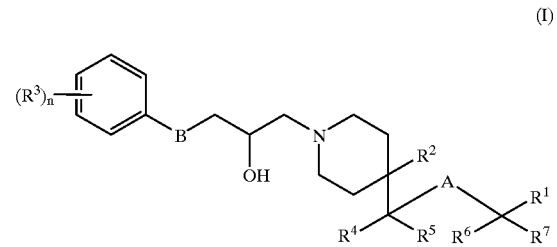

(I)

wherein
R¹ and R² each independently represents a phenyl group optionally substituted by 1, 2 or 3 groups selected from C₁₋₆alkyl, C₂₋₆alkenyl, C₂₋₆alkynyl, cycloC₃₋₇alkyl, cycloC₃₋₇alkylC₁₋₄alkyl, cycloC₃₋₇alkoxy, fluoroC₁₋₆alkyl, C₁₋₆alkoxy, fluoroC₁₋₆alkoxy, hydroxy, phenoxy, halo, cyano, nitro, —SRᵃ, —SORᵃ, —SO₂Rᵃ, —NRᵃRᵇ, —NRᵃCORᵇ, —NRᵃCO₂Rᵇ, —CORᵃ, —CO₂Rᵃ— or —CONRᵃRᵇ;
R³ represents halogen, cyano, nitro, C₁₋₈alkyl, C₂₋₆alkenyl, C₂₋₆alkynyl, cycloC₃₋₇alkyl, cycloC₃₋

7alkylC$_{1-4}$alkyl, cycloC$_{3-7}$alkoxy, fluoroC$_{1-6}$alkyl, C$_{1-6}$alkoxy, fluoroC$_{1-6}$alkoxy, hydroxy, hydroxyC$_{1-6}$alkyl, hydroxyC$_{1-6}$alkoxy, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$, —CONR$^a$R$^b$, adamantyl, morpholinyl (optionally substituted by one or two C$_{1-4}$alkyl groups), phenyl, plienoxy, phenylazo, benzyl or benzyloxy, wherein said phenyl or the phenyl moiety of said phenoxy, phenylazo or benzyloxy groups is optionally substituted by one or two substituents selected from halogen, C$_{1-4}$alkyl, C$_{1-4}$alkoxy or hydroxy; or, when n is 2, 3, 4 or 5 two groups R$^3$ on adjacent carbon atoms are linked by —OCH$_2$O—, —OCH$_2$CH$_2$O—, —CH$_2$CH$_2$CH$_2$—, —CH$_2$CH=CH—, —NR$^a$—CH=CH— or —OC(R$^a$)$_2$CH$_2$C(O)—;

R$^4$, R$^5$, R$^6$, and R$^7$ each independently represents hydrogen or C$_{1-6}$alkyl;

R$^a$ and R$^b$ each independently represents hydrogen, C$_{1-6}$alkyl, phenyl or trifluoromethyl;

A represents —O— or —S—;

B represents —O—, —S—, —NR$^a$— or —CHR$^a$—; and n is zero, 1, 2, 3, 4 or 5;

or a pharmaceutically acceptable salt or a prodrug thereof.

2. A compound as claimed in claim 1 wherein A represents —O— or —S—.

3. A compound as claimed in claim 1 wherein B represents —O—, —S—, —NH—, —NCH$_3$— or —CH$_2$.

4. A compound as claimed in claim 1 wherein R$^4$, R$^5$, R$^6$ and R$^7$ each independently represents hydrogen or C$_{1-6}$alkyl.

5. A compound as claimed in claim 1 wherein R$^1$ represents phenyl or phenyl substituted by 1, 2 or 3 substituents selected from nitro, trifluoromethyl, bromo, chloro, fluoro, iodo, cyano, methyl, ethyl, cyclopropyl, tert-butyl, vinyl, methoxy, phenoxy, and amino.

6. A compound as claimed in claim 1 wherein R$^2$ represents phenyl or phenyl substituted by a halogen atom.

7. A compound as claimed in claim 1 wherein R$^3$ is selected from halogen, cyano, nitro, C$_{1-8}$alkyl, C$_{2-4}$alkenyl, fluoroC$_{1-3}$alkyl, fluoroC$_{1-3}$alkoxy, C$_{1-6}$alkoxy, hydroxyC$_{2-3}$alkoxy, NR$^a$COR$^b$, —CO$_2$R$^a$, adamantyl, 2,6-dimethylmorpholino, phenyl, phenoxy, phenylazo or benzyloxy, wherein said phenyl group or the phenyl moiety of said phenoxy, phenylazo, or benzyloxy group is unsubstituted or substituted by C$_{1-4}$alkyl, or when n is 2, 3, 4 or 5, two groups R$^3$ on adjacent carbon atoms are linked by —OCH$_2$O—, —CH$_2$CH$_2$CH$_2$—, —NHCH=CH— or —OC(CH$_3$)$_2$CH$_2$C(O)—.

8. A compound as claimed in claim 1 wherein n is 1 or 2 and R$^3$ is selected from fluoro, chloro, cyano, methyl, methoxy, —OCH$_2$CH$_2$OH or —NHCOCH$_3$ or n is 3 wherein two groups R$^3$ on adjacent carbon atoms are linked by —CH$_2$CH$_2$CH$_2$— and the other group R$^3$ is bromine, or n is 5 and R$^3$ is selected from fluoro and trifluoromethyl.

9. A compound as claimed in claim 1 wherein n is zero or 1 and R$^3$ is selected from fluoro, ethyl, phenyl, phenoxy or 2,6-dimethylmorpholino, or n is 2 and R$^3$ is selected from fluoro, methoxy and cyano, or n is 3 wherein two groups R$^3$ on adjacent carbon atoms are linked by —OC(CH$_3$)$_2$CH$_2$C(O)— and the other group R$^3$ is chlorine.

10. A compound as claimed in claim 1 wherein n is 1 or 2 and R$^3$ is selected from chloro, bromo, methyl, t-butyl, allyl, adamantyl, cumyl or two groups R$^3$ on adjacent carbon atoms are linked by —OCH$_2$O—.

11. A compound of the formula (IA):

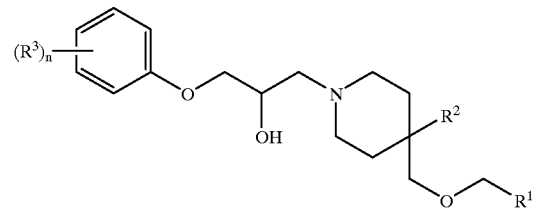

(IA)

wherein R$^1$, R$^2$, R$^3$ and n are as defined in claim 1;

or a pharmaceutically acceptable salt or prodrug thereof.

12. A compound as claimed in claim 11 wherein R$^1$ represents phenyl or phenyl substituted by 1, 2 or 3 substituents selected from nitro, trifluoromethyl, bromo, chloro, fluoro, iodo, cyano, methyl, ethyl, cyclopropyl, tert-butyl, vinyl, methoxy, phenoxy, and amino.

13. A compound as claimed in claim 11 wherein R$^2$ represents phenyl or phenyl substituted by a halogen atom.

14. A compound as claimed in claim 11 wherein R$^3$ is selected from halogen, cyano, nitro, C$_{1-8}$alkyl, C$_{2-4}$alkenyl, fluoroC$_{1-3}$alkyl, fluoroC$_{1-3}$alkoxy, C$_{1-6}$alkoxy, hydroxyC$_{2-3}$alkoxy, NR$^a$COR$^b$, —CO$_2$R$^a$, adamantyl, 2,6-dimethylmorpholino, phenyl, phenoxy, phenylazo or benzyloxy, wherein said phenyl group or the phenyl moiety of said phenoxy, phenylazo, or benzyloxy group is unsubstituted or substituted by C$_{1-4}$alkyl, or when n is 2, 3, 4 or 5, two groups R$^3$ on adjacent carbon atoms are linked by —OCH$_2$O—, —CH$_2$CH$_2$CH$_2$—, —NHCH=CH— or —OC(CH$_3$)$_2$CH$_2$C(O)—.

15. A compound as claimed in claim 11 wherein n is 1 or 2 and R$^3$ is selected from fluoro, chloro, cyano, methyl, methoxy, —OCH$_2$CH$_2$OH or —NHCOCH$_3$ or n is 3 wherein two groups R$^3$ on adjacent carbon atoms are linked by —CH$_2$CH$_2$CH$_2$— and the other group R$^3$ is bromine, or n is 5 and R$^3$ is selected from fluoro and trifluoromethyl.

16. A compound as claimed in claim 11 wherein n is zero or 1 and R$^3$ is selected from fluoro, ethyl, phenyl, phenoxy or 2,6-dimethylmorpholino, or n is 2 and R$^3$ is selected from fluoro, methoxy and cyano, or n is 3 wherein two groups R$^3$ on adjacent carbon atoms are linked by —OC(CH$_3$)$_2$CH$_2$C(O)— and the other group R$^3$ is chlorine.

17. A compound as claimed in claim 11 wherein n is 1 or 2 and R$^3$ is selected from chloro, bromo, methyl, t-butyl, allyl, adamantyl, cumyl or two groups R$^3$ on adjacent carbon atoms are linked by —OCH$_2$O—.

18. A compound of the formula (IB):

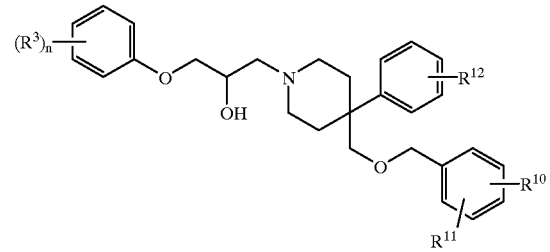

(IB)

wherein
R³ and n are as defined in claim 1;
R¹⁰ and R¹¹ each independently represent hydrogen, halogen, $C_{1-6}$alkyl or trifluoromethyl; and
R¹² represents hydrogen or halogen;
or a pharmaceutically acceptable salt or prodrug thereof.

19. A compound as claimed in claim 18 wherein R³ is selected from halogen, cyano, nitro, $C_{1-8}$alkyl, $C_{2-4}$alkenyl, fluoro$C_{1-3}$alkyl, fluoro$C_{1-3}$alkoxy, $C_{1-6}$alkoxy, hydroxy$C_{2-3}$ alkoxy, NR$^a$COR$^b$, —CO₂R$^a$, adamantyl, 2,6-dimethylmorpholino, phenyl, phenoxy, phenylazo or benzyloxy, wherein said phenyl group or the phenyl moiety of said phenoxy, phenylazo, or benzyloxy group is unsubstituted or substituted by $C_{1-4}$alkyl, or when n is 2, 3, 4 or 5, two groups R³ on adjacent carbon atoms are linked by —OCH₂O—, —CH₂CH₂CH₂—, —NHCH=CH— or —OC(CH₃)₂CH₂C(O)—.

20. A compound as claimed in claim 18 wherein n is 1 or 2 and R³ is selected from fluoro, chloro, cyano, methyl, methoxy, —OCH₂CH₂OH or —NHCOCH₃ or n is 3 wherein two groups R³ on adjacent carbon atoms are linked by —CH₂CH₂CH₂— and the other group R³ is bromine, or n is 5 and R³ is selected from fluoro and trifluoromethyl.

21. A compound as claimed in claim 18 wherein n is zero or 1 and R³ is selected from fluoro, ethyl, phenyl, phenoxy or 2,6-dimethylmorpholino, or n is 2 and R³ is selected from fluoro, methoxy and cyano, or n is 3 wherein two groups R³ on adjacent carbon atoms are linked by —OC(CH₃)₂CH₂C(O)— and the other group R³ is chlorine.

22. A compound as claimed in claim 18 wherein n is 1 or 2 and R³ is selected from chloro, bromo, methyl, t-butyl, allyl, adamantyl, cumyl or two groups R³ on adjacent carbon atoms are linked by —OCH₂O—.

23. A compound as claimed in claim 1 selected from:
3-(3-acetamidophenyloxy)-1-[4-phenyl-4-[3,5-bis(trifluoromethyl)benzyloxymethyl]piperidine]-propan-2-ol;
3-(3-phenyloxy)-1-[4-phenyl-4-[3,5-bis(trifluoromethyl)benzyloxymethyl]piperidine]-propan-2-ol;
3-(3,5-dimethylphenyloxy)-1-[4-phenyl-4-[3,5-bis(trifluoromethyl)benzyloxymethyl]piperidine]-propan-2-ol;
3-(4-methoxyphenyloxy)-1-[4-phenyl-4-[3,5-bis(trifluoromethyl)benzyloxymethyl]piperidine]-propan-2-ol;
3-(4-chlorophenyloxy)-1-[4-phenyl-4-[3,5-bis(trifluoromethyl)benzyloxymethyl]piperidine]-propan-2-ol;
3-(3,4-dimethylphenyloxy)-1-[4-phenyl-4-[3,5-bis(trifluoromethyl)benzyloxymethyl]piperidine]-propan-2-ol;
3-(4-fluorophenyloxy)-1-[4-phenyl-4-[3,5-bis(trifluoromethyl)benzyloxymethyl]piperidine]-propan-2-ol;
3-(3-ethylphenyloxy)-1-[4-phenyl-4-[3,5-bis(trifluoromethyl)benzyloxymethyl]piperidine]-propan-2-ol;
3-(2-cyanophenyloxy)-1-[4-phenyl-4-[3,5-bis(trifluoromethyl)benzyloxymethyl]piperidine]-propan-2-ol;
1-[4-phenyl-4-[3,5-bis(trifluoromethyl)benzyloxymethyl]piperidine]-3-(4-trifluoromethoxyphenyloxy)-propan-2-ol;
or a pharmaceutically acceptable salt thereof.

24. A pharmaceutical composition comprising a compound as claimed in claim 1, together with at least one pharmaceutically acceptable carrier or excipient.

25. A method for the treatment or prevention of depression and/or anxiety which method comprises administration to a patient in need of such treatment a therapeutically effective amount of a compound according to claim 1.

26. A method for the treatment or prevention of physiological disorders associated with an excess of tachykinins, which method comprises administration to a patient in need thereof of a tachykinin reducing amount of a compound according to claim 1.

27. A method according to claim 26 for the treatment or prevention of pain or inflammation, migraine, emesis or postherpetic neuralgia.

28. A process for the preparation of a compound as claimed in claim 1 which comprises:
(A), reaction of an epoxide of formula (II) with a piperidine of formula (III):

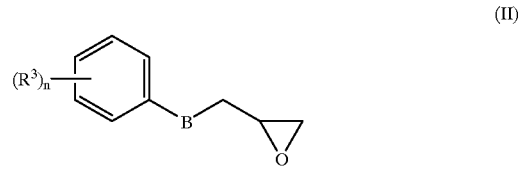

(II)

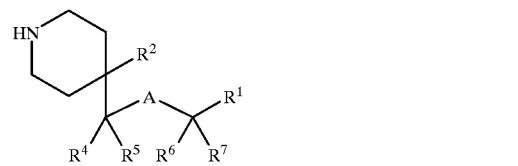

(III)

wherein A, B, R¹, R², R³, R⁴, R⁵, R⁶, R⁷ and n are as defined in claim 1; or (B), where B is other than —CHR$^a$—, reaction of a compound of formula (IV) with a compound of formula (VI) in the presence of base:

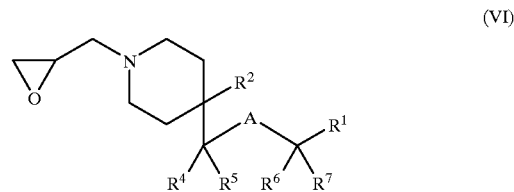

(VI)

wherein A, R¹, R², R⁴, R⁵, R⁶ and R⁷ are as defined in claim 1; or (C), where B represents —CHR$^a$—, reaction of a compound of formula (VI) with a compound of formula (VII):

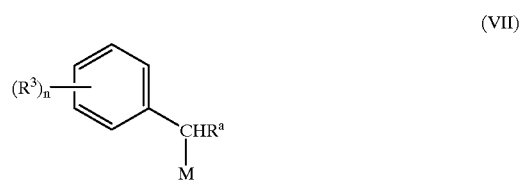

(VII)

wherein R³, n and R$^a$ are defined in claim 1, and M represents Li or MgHal where Hal represents chlorine, bromine or iodine;

each process being followed, where necessary, by the removal of any protecting group where present;

and when the compound of formula (I) is obtained as a mixture of enantiomers or diastereoisomers, optionally resolving the mixture to obtain the desired enantiomer; and/or, if desired, converting the resulting compound of formula (I) or a salt thereof, into a pharmaceutically acceptable salt thereof.

* * * * *